United States Patent [19]

Charudattan

[11] 4,263,036

[45] Apr. 21, 1981

[54] METHOD AND COMPOSITION FOR CONTROLLING HYDRILLA

[75] Inventor: Raghavan Charudattan, Gainesville, Fla.

[73] Assignee: Board of Reagents, State of Florida, Gainesville, Fla.

[21] Appl. No.: 9,386

[22] Filed: Feb. 2, 1979

[51] Int. Cl.³ .............................................. A01N 63/04
[52] U.S. Cl. ........................................... 71/66; 71/67; 71/79
[58] Field of Search ....................................... 71/79, 66

[56] References Cited

U.S. PATENT DOCUMENTS

| | | | |
|---|---|---|---|
| 3,849,104 | 11/1974 | Daniel et al. | 71/79 |
| 3,999,973 | 12/1976 | Templeton | 71/79 |
| 4,097,261 | 6/1978 | Conway et al. | 71/66 |

*Primary Examiner*—Glennon H. Hollrah
*Attorney, Agent, or Firm*—Arthur G. Yeager

[57] ABSTRACT

Growth of *Hydrilla verticillata* is controlled by application of the microorganism *Fusarium roseum* "Culmorum" in amounts of 25,000 to 100,000 conidia per ml.

9 Claims, No Drawings

METHOD AND COMPOSITION FOR CONTROLLING HYDRILLA

BACKGROUND OF THE INVENTION

It is estimated that a fifth of all fresh water ponds, lakes and rivers in Florida is infested with *Hydrilla verticillata* L. F. Royle (Hydrocharitaceae), and the weed is spreading rapidly. Since its introduction into Florida waters around 1960, this weed has moved to several other states in the U.S.A. Serious economic losses and ecologic damages resulting from this submerged weed have spurred research on biological, chemical and mechanical controls. Among biological agents researched are plant pathogens; however, very few diseases of submerged weeds are known and those found on Hydrilla have not been sufficiently damaging or specific to this host to promote their use in the field.

In 1974, a disease of *Stratiotes aloides* L. (Hydrocharitaceae) in Holland was noted in which mature plants had symptoms of root- and crown-rots and severely diseased plants appeared to sink gradually as a consequence of tissue decay. A few infected plant parts were studied and a group of fungi were cultured from the plants including a *Fusarium roseum* "Culmorum" (Lk. ex Fr.) Synd. & Hans. In view of the close taxonomic relationship between *Stratiotes aloides* and *Hydrilla verticillata* it was considered that these fungi might be effective on *Hydrilla verticillata*. Among the many fungal isolates obtained from *S. aloides*, only "Culmorum" was capable of killing Hydrilla. Results prove that the Dutch "Culmorum" is a virulent pathogen of Hydrilla unlike most other fusaria tested on this host, and that it is effective in the control of Hydrilla in Florida.

DETAILED DESCRIPTION OF THE INVENTION

The effects of the "Culmorum" isolate on Hydrilla were determined in three test systems. The first one consisted of incubating 8 to 10 cm long terminal portions of Hydrilla shoots in $3 \times 15$ cm glass tubes with 40 ml of sterile water to which were added dense macroconidial suspensions. Control tubes were without conidia. Fungal inocula, consisting of filtered macroconidial suspension obtained from potato dextrose agar cultures, were quantitated with a hemacytometer. Inoculum levels were between 2500 and 250,000 conidia per ml (100,000 and 10 million conidia per tube containing 40 ml of water). Inoculated and control Hydrilla tubes were incubated under diffuse light at $22° \pm 2°$ C. for several weeks. Damage to Hydrilla from the Dutch 'Culmorum' was usually evident as chlorosis and discoloration of inoculated shoots 10 to 14 days after inoculation. In 3 weeks, death and lysis or regrowth of partially damaged Hydrilla were observed. The threshold of inoculum needed to damage Hydrilla was found to be 1 million conidia per tube or 25,000 per ml. A dose and effect relationship was seen on inoculated Hydrilla; at lower inoculum levels the shoots were only partially damaged or killed while at higher inoculum levels, e.g. 250,000 per ml, the effects were drastic and lethal.

In the second system, 20 l aquarium tanks were layered with river sand, filled with 14 l of water and planted with 100 terminal ends of Hydrilla shoots, each with an active growing bud. After two days, the tanks were inoculated with conidial suspensions of Culmorum at approximately 80,000 or 90,000 conidia per ml of water in tanks. Three weeks after inoculation, Hydrilla shoots started to discolor and developed signs of rotting. In about 5 weeks, the shoots broke down completely, and some that were still green were defoliated and uprooted, and floated to the water surface.

In the third system, the fungus was grown for two weeks on a sterilized mixture of 9 parts sand, 1 part oat meal and 3 parts water, and mixed with the bottom sand in Hydrilla tubes at 1:1 and 1:10 proportions (w/w) of inoculum and sand. Controls had sand-oat-water mixture without the fungus, mixed with an equal weight of sand. A Hydrilla plant with shoots, roots and at least one tuber was planted per inoculated and control tubes. After a week, the inoculated plants turned pale and were dead by the end of 14 days.

In all these systems, the inoculated fungus could be reisolated from inoculated, dead, dying or green Hydrilla shoots after surface sterilization and plating on potato dextrose agar. Controls did not yield the fungus. In addition, the conidia were observed to germinate on, and penetrate into Hydrilla tissue which confirmed that pathogenic capability of the fungus.

The following examples illustrate various features and embodiments of this invention.

EXAMPLE 1

In order to decide that the effects of the "Culmorum" isolate on Hydrilla were specifically due to its infectivity and not due merely to massive numbers of fungal spores in water, a comparative inoculation test was set up. In this test, three unidentified Fusarium spp., isolated from Hydrilla in Florida, a *F. roseum* from *Ficus elastica* Roxb. and a *F. roseum* "Graminearum" from *Eichhornia crassipes*—(Mart.) Solms in Florida were included. The test tube procedure described first was used, with inoculum densities between 2500 and 250,000 conidia per ml of treated water.

The results confirmed that the Dutch "Culmorum" was indeed unique in its effects on Hydrilla and Ficus isolate of *F. roseum* did not damage Hydrilla even at higher levels of inoculum. The "Graminearum" from *E. crassipes* was capable of damaging Hydrilla, inciting similar symptoms as the Dutch Culmorum. However, the threshold of inoculum needed to cause damage by this isolate was approximately 60,000 conidia per ml, or 2.4 times higher than that of Culmorum. The Dutch Culmorum isolate hence was not only pathogenic to Hydrilla but also was more virulent than any Fusarium tested.

EXAMPLE 2

Conidia and mycelial fragments of the Florida isolate of "Graminearum" from *E. crassipes* were applied either as suspension or was injected into bottom sand around 25 rooted Hydrilla shoots maintained in 4 l glass jars under 2.5 l of water. For inoculum, the fungus was grown on potato dextrose broth for a week. About 30 g of wet, filtered mycelium and conidia were blended in 125 ml of sterile water. The resulting slurry was applied with an 100 ml hypodermic syringe, fitted with a blunt needle, at 10, 20, and 40 ml portions consisting of 0.96 g, 1.92 g and 3.84 g of conidia and mycelium per l. The inoculum was suspended over Hydrilla in water or injected into the soil. Control plants received equal amounts of sterile water. Inoculum applied as suspension caused considerable turbidity to water but also was effective in killing most of the Hydrilla by 3 weeks. In jars with soil-injected inoculum, some damage and death of Hydrilla shoots were visible, but mostly the plants were healthy, similar to the controls.

EXAMPLE 3

Since the Dutch isolate is subject to quarantine due to its foreign origin, the effects of the local "Graminearum" isolate were tested in an outdoor, large scale test. Plastic swimming pools of 3.04 m diameter and 0.76 m height were layered with river sand, each was planted with 45 kg of fresh Hydrilla, and filled with irrigation water. After five weeks, pools were inoculated with mycelial homogenates. One pool was inoculated with a suspension of approximately 0.18 g/l of conidia and mycelium and a second pool at 1 g/l. Control pools were maintained. There were isolated patches of dead Hydrilla a month following inoculation, but no appreciable control of this plant was achieved in pools.

EXAMPLE 4

Host range of the Dutch Culmorum to a few common aquatic plants of Florida and a limited number of crop hosts has been tested. Rooted aquatic plants in glass containers were screened, using inoculum of 125,000 conidia per ml. At this level, the isolate was lethal to *Ceratophyllum demersum* L. (Ceratophyllaceae); *Egeria densa* Planchon, and *Vallisneria americana* Michx. (both of Hydrocharitaceae) and *Najas quadalupensis* (Spreng.) Magnus (Najadaceae). On *E. crassipes*, it caused severe root rot. *Alternanthera philoxeroides* (Mart.) Griseb. (Amaranthaceae); *Nuphar luteum* (L.) Sibthorp. & Smith (Nymphaeaceae); and *Ruppia maritima* L. (Ruppiaceae) were not affected by this isolate.

In preemergence infectivity trials using ca. 38,000 conidia/g of soil, the Culmorum did not depress germination of seeds or caused seedling blights on bean (*Phaseolus vulgaris* L. var. Pole, Blue Lake.); celery (*Apium graveolens* L., var. dulce DC., var. Pascal); corn (*Zea mays* L., var. Silver Queen); lettuce (*Lactuca sativa* L., var. Bibb); pepper (*Capsicum annum* var. Yolo); sorghum (*Sorghum vulgare* Pers., var. unknown); and soybean (*Glycine max* Merr., var. Forrest).

Several hundred fungi and bacteria have been tested in the past for pathogenicity to Hydrilla. To date no other *F. roseum* Culmorum or another pathogen possessing virulence comparable to Culmorum has been discovered in the U.S.A. or elsewhere. The Dutch Culmorum appears to be the most effective pathogen of Hydrilla known today.

The amount of the microorganism *F. roseum* Culmorum needed to effectively control *Hydrilla verticillata* is from about 25,000 to about 100,000 conidia per ml of water.

This herbicide may be utilized effectively in diverse formulations, including the agronomically acceptable adjuvants and carriers normally employed for facilitating the dispersion of active ingredients for agriculture applications recognizing a known fact that the dosage, formulations, mode of application of a chemical agent and other variables may affect its activity in any given application. Thus, the previously described herbicide may be formulated as a suspension or dispersion, in aqueous or non-aqueous media, as a dust, as a wettable powder, as an emulsifiable concentrate, as a granule, or as any of several other known types of formulations, depending on the desired mode of application. These herbicide compositions may be applied as sprays, dust, or granules to the plant situs against which herbicidal activity is desired.

In order to provide compositions in the form of dust, granules, water dispersible powders, aqueous dispersions, or emulsions and dispersions in organic liquids, the carrier or diluent agent in such formulations may be a finely divided solid, an organic liquid, water, a wetting agent, a dispersing agent, or emulsifying agent, or any suitable combination of these. Generally, when liquids and wettable powders are prepared a conditioning agent comprising one or more surface-active agents or surfactants is present in amounts sufficient to render a given composition containing the active material, the microorganism, dispersible in water or in oil. The microorganism, the fungus *Fusarium roseum* Culmorum is obtained by conventional submerged culture fermentations. To convert it to a form which will facilitate the preparation of the following described compositions, a slurry is prepared which is then dried onto a primary agronomically acceptable carrier such as vermiculite, whereby the microorganism is adsorbed onto the carrier, becomes the concentrate for preparing the desired composition. If desired, the slurry can be used as the concentrate for herbicidal composition.

The surface active agent used in the invention can be a wetting dispersing or emulsifying agent which will assist dispersion of the effective composition. The surface-active agent or surfactant can include such anionic, cationic and non-ionic agents as have heretofore been generally employed in plant control compositions of similar type. Suitable surface-active agents are set forth, for example, in "Detergents and Emulsifiers" 1971 Annual by John W. McCutcheon, Inc.

In general, 1–10% by weight of the surface-active agent will be used in compositions of this invention and ordinarily the amount of surface-active agent will range from 1–5% but may even be less than 1% by weight.

Additional surface-active agents can be added to formulations to increase the ratio of surfactants: active ingredients up to as high as 5:1 by weight. Such compositions may have a greater biological effectiveness than can be expected when the components are used separately. When used at higher ratios, it is preferred that the surfactant be present in the range of one-fifth to five parts surfactant for each one part of active agent.

The following are more detailed formulations exemplifying the various compositions.

EXAMPLE 5

Wettable powders are water-dispersible compositions containing the active material, an inert solid extender, and one or more surfactants to provide rapid wetting and to prevent heavy flocculations when suspended in water.

The inert extenders which are preferred for use in the wettable powders of this invention containing the active compounds are of mineral origin.

Extenders suitable for the wettable powder formulations of this invention are the nature clays, diatomaceous earth and synthetic mineral fillers derived from silica and silicate. Most preferred fillers for this invention are kaolinites, attapulgite clay, montmorillonite clays, synthetic silicas, synthetic magnesium silicate and calcium sulfate dihydrate.

Among the more preferred surfactants are the non-ionic and anionic types. They are most suitable for the preparation of dry, wettable products of this invention and dispersants. Occasionally a liquid, non-ionic compound which is primarily an emulsifier, may serve as both wetter and dispersant.

Most preferred wetting agents are alkylbenzene and alkylnapthalene sulfonates, sulfated fatty alcohols, amines or acid amides, long chain esters of sodium isethionate, esters of sodium sulfosuccinate, sulfated or sulfonated vegetable oils, and ditertiary acetylenic glycols. Preferred dispersants are methyl cellulose, polyvinyl alcohol, lignin sulfonates, polymeric alkylnapthalene sulfonates, sodium naphthalene sulfonates, polymethylene bisnaphthalene sulfonate and sodium-N-methyl-N-(long chain acid) taruates.

Wetting and dispersing agents in these preferred wettable power compositions of the invention are usually present at concentrations of from about 0.5 weight percent to 5 weight percent. The inert extender then completes the formulation. Where needed, 0.1 weight percent of the extender may be replaced by a corrosion inhibitor or an anti-foaming agent or both.

Thus, wettable powder contains a corrosion inhibitor or an anti-foaming agent or both, the corrosion inhibitor should not exceed about 1 percent of the composition, and the anti-foaming agent should not exceed about 0.5 percent by weight of the composition, both replacing equivalent amounts of the inert extender.

EXAMPLE 6

Dusts are dense powder compositions which are intended for application in dry form. Dusts are characterized by their free-flowing and rapid settling properties so that they are not readily windborn to areas where their presence is not desired. They contain primarily an active ingredient and a dense, free-flowing, solid extender. Their performance is sometimes aided by the inclusion of a wetting agent and convenience in manufacture frequently demands the inclusion of an inert absorptive grinding aid.

The wettable powder as described above can also be used in the preparation of dusts. While such wettable powders can be used directly in dust form, it is more advantageous to dilute them by blending with the dense dust diluent. In this manner, dispersing agents, corrosion inhibitors, and anti-foam agents may also be used as components of a dust.

Thus, the dust compositions of this invention can comprise from about 0.5 to 20.0 weight percent active ingredient, 5 to 25 weight percent filler, 0 to 1.0 weight percent wetting agent and from about 30 to 90 weight percent dense, free-flowing extender, as these terms are used herein. Such dust formulations can contain, in addition, minor amounts of dispersants, corrosion inhibitors, and anti-foam agents derived from the wettable powders used to make the dust.

EXAMPLE 7

Emulsifiable oils are usually solutions or suspensions of active material in non-water miscible solvents together with a surfactant and/or emulsifier.

For compositions of this invention, emulsifiable oil compositions can be made by mixing the active ingredient with an organic solvent and surfactant. Suitable solvents for the compositions of this invention are chlorinated solvents, water immiscible ethers, esters, or ketones alone or in admixture with aromatic hydrocarbons. Suitable surfactants are those ionic or non-ionic agents known to the art as emulsifying agents.

Emulsifying agents most suitable for the emulsifiable oil compositions of this invention are long chain alkyl or mercaptan polyethoxy alcohols, alkylaryl polyethoxy alcohols, sorbitan fatty acid esters, polyoxyethylene ethers with sorbitan fatty acid esters, polyethylene glycol esters with fatty rosin acids, fatty alkylol amide condensates, calcium and amine salts of fatty alcohol sulfates, oil soluble petroleum sulfonates, or preferably mixtures of these emulsifying agents should comprise from about 1 to 10 weight percent of the total composition. As described above, however, up to 5 parts of emulsifying agent for each part of active ingredient can be used.

Thus, emulsifiable oil compositions of the present invention can consist of from about 10 to 50 weight percent active ingredient, about 40 to 82 percent solvents, and about 1 to 10 weight percent emulsifier, as these terms are defined and used above.

EXAMPLE 8

Granules are physically stable, particulate compositions containing spores and-or mycelium of this invention which adhere to or are distributed through a basic matrix of a coherent, inert carrier with microscopic dimensions. In order to aid leaching of the active ingredient from the granule, a surfactant can be present.

The inert carrier is preferably of mineral origin, and suitable carriers are natural clays, some pyrophyllites and vermiculite. Suitable wetting agents can be anionic or non-ionic.

For the granule compositions of this invention, most suitable carriers are to two types. The first are porous, absorptive pre-formed granules, such as preformed and screened granular attapulgite or heat expanded, granular, screened vermiculite. On either of these, a solution of the active agent can be sprayed and will be absorbed at concentrations up to 25 weight percent of the total weight. The second type are initially powdered kaolin clays, hydrated attapulgite or bentonite clays in the form of sodium, calcium or magnesium bentonites. Water-soluble salts such as sodium salts may also be present to aid in the disintegrations of the granules in the presence of moisture. These ingredients are blended with the active components to give mixtures that are granulated, followed by drying to yield formulations with the active component distributed uniformly throughout the mass. Such granules can also be made with 25 to 30 weight percent active component but more frequently a concentration of about 10 weight percent is desired for optimum distribution. The granular compositions of this invention are believed to be most useful in a size range of 15–30 mesh.

The most suitable wetting agents for the granular compositions of this invention depend upon the type of granule used. When pre-formed granules are sprayed with active material in liquid form, the most suitable wetting agents are non-ionic, liquid wetters miscible with the solvent. These are more generally known in the art as emulsifiers and comprise alkylaryl polyether alcohols, alkyl polyether alcohols, polyoxyethylene sorbitan fatty acid esters, polyethylene glycol esters with fatty or rosin acids, fatty alkylol amide condensates, oil soluble petroleum or vegetable oil sulfonates, or mixtures of these. Such agents will usually comprise up to about 5 weight percent of the total composition.

When the active ingredient is first mixed with a powdered carrier and subsequently granulated, liquid nonionic wetters can still be used, but it is usually preferable to incorporate at the mixing stage, one of the solid, powdered anionic wetting agents such as those previously listed for the wettable powders. Such agents should comprise about 0 to 2 percent of the total composition.

Thus the preferred granular formulation of this invention comprise about 5 to 30 weight percent active material, about 0 to 5 weight percent wetting agent, and about 65 to 95 percent inert mineral carrier, as these terms are used herein.

What is claimed as new and what it is desired to secure by Letters Patent of the United States is:

1. A herbicidal concentrate for the preparation of compositions effective to control *Hydrilla verticillata* comprising an effective amount of the microorganism *Fusarium roseum* Culmorum adsorbed on an agronomically acceptable carrier.

2. A herbicidal concentrate of claim 1 in which the concentrate is a slurry of the said microorganism.

3. A herbicidal composition for the control of *Hydrilla verticillata* comprising an effective amount of the microorganism *Fusarium roseum* Culmorum and an agronomically acceptable carrier.

4. A wettable powder composition useful in the control of *Hydrilla verticillata* comprising
   25-90% of the microorganism *Fusarium roseum* Culmorum
   0.5-2% of a wetting agent,
   0.25-5% of a dispersant, and
   9-75% inert extender.

5. A dust composition useful in the control of *Hydrilla verticillata* comprising:
   0.5-20% of the microorganism *Fusarium roseum* Culmorum,
   5-25% of a dense filler,
   0-1% of a wetting agent, and
   30-90% of an extender.

6. An emulsifiable oil composition useful in the control of *Hydrilla verticillata* comprising:
   10-50% of the microorganism *Fusarium roseum* Culmorum,
   40-82% of a suitable solvent, and
   1-10% of an emulsifier.

7. A granule composition useful in the control of *Hydrilla verticillata* comprising:
   5-30% of the microorganism *Fusarium roseum* Culmorum,
   0-5% of a wetting agent, and
   65-95% of an inert carrier.

8. A method for controlling the growth of *Hydrilla verticillata* comprising treating said Hydrilla with an amount of a microorganism comprising *Fusarium roseum* Culmorum effective to infect and kill said Hydrilla.

9. The method of claim 8 wherein the microorganism is applied to said Hydrilla in the amount of 25,000 to 250,000 conidia/ml of water.